(12) United States Patent
Patel et al.

(10) Patent No.: US 12,089,844 B2
(45) Date of Patent: Sep. 17, 2024

(54) ACTUATION MECHANISMS FOR SURGICAL INSTRUMENTS

(71) Applicant: INTUITIVE SURGICAL OPERATIONS, INC., Sunnyvale, CA (US)

(72) Inventors: Atal Patel, Mission Viejo, CA (US); Matt Wixey, San Jose, CA (US); Ashley Wellman, East Palo Alto, CA (US)

(73) Assignee: INTUITIVE SURGICAL OPERATIONS, INC.

( * ) Notice: Subject to any disclaimer, the term of this patent is extended or adjusted under 35 U.S.C. 154(b) by 202 days.

(21) Appl. No.: 17/414,741

(22) PCT Filed: Dec. 6, 2019

(86) PCT No.: PCT/US2019/064861
§ 371 (c)(1),
(2) Date: Jun. 16, 2021

(87) PCT Pub. No.: WO2020/131418
PCT Pub. Date: Jun. 25, 2020

(65) Prior Publication Data
US 2022/0071632 A1 Mar. 10, 2022

Related U.S. Application Data

(60) Provisional application No. 62/783,460, filed on Dec. 21, 2018.

(51) Int. Cl.
*A61B 17/072* (2006.01)
*A61B 34/37* (2016.01)

(52) U.S. Cl.
CPC ........ *A61B 17/07207* (2013.01); *A61B 34/37* (2016.02); *A61B 2017/07257* (2013.01);
(Continued)

(58) Field of Classification Search
CPC .... A61B 17/07207; A61B 2017/07257; A61B 2017/07271; A61B 2017/07278;
(Continued)

(56) References Cited

U.S. PATENT DOCUMENTS 4,305,539 A 12/1981 Korolkov et al.
4,319,576 A 3/1982 Rothfuss
(Continued)

FOREIGN PATENT DOCUMENTS

EP 0277532 B1 8/1990
EP 0277529 B1 4/1993
(Continued)

OTHER PUBLICATIONS

International Search Report and Written Opinion for Application No. PCT/US2021/012284, mailed May 6, 2021, 23 pages.
(Continued)

*Primary Examiner* — Stephen F. Gerrity
*Assistant Examiner* — Linda J Hodge
(74) *Attorney, Agent, or Firm* — Farber LLC

(57) ABSTRACT

The present disclosure provides a surgical instrument, such as a tissue sealing instrument, with an elongate shaft and an end effector. The end effector includes a first jaw and a second jaw that includes a staple cartridge with a plurality of staples for engaging tissue. The instrument further includes a drive member for closing the jaws and engaging the staples, and an actuation mechanism, such as a coil, in contact with the drive member. The actuation mechanism is configured to translate the drive member distally through the first jaw (instead of through the staple cartridge as in conventional surgical stapling instruments). Eliminating the internal channel for the actuation coil from the staple cartridge provides more space in the cartridge for the staples,
(Continued)

allowing for the use of taller staples and/or a more compact and maneuverable instrument.

13 Claims, 15 Drawing Sheets

(52) U.S. Cl.
CPC .............. *A61B 2017/07271* (2013.01); *A61B 2017/07278* (2013.01)

(58) Field of Classification Search
CPC ........... A61B 2017/07285; A61B 2017/00477; A61B 2017/00486; A61B 2017/2908; A61B 2017/2927; A61B 34/30; A61B 34/37; A61B 2034/305; A61B 2034/306; A61B 1/00112; A61B 1/00119; A61B 1/00128; H02K 7/003; Y10T 74/20329
USPC .......................................... 227/175.1–182.1
See application file for complete search history.

(56) References Cited

U.S. PATENT DOCUMENTS

| | | |
|---|---|---|
| 4,407,286 A | 10/1983 | Noiles et al. |
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A * | 10/1996 | Bishop ............... A61B 17/0682 227/19 |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A | 7/1997 | Conway et al. |
| 5,667,626 A | 9/1997 | Cayford et al. |
| 5,673,842 A | 10/1997 | Bittner et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,700,270 A | 12/1997 | Peyser et al. |
| 5,700,276 A | 12/1997 | Benecke |
| 5,709,680 A | 1/1998 | Yates et al. |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,050,996 A | 4/2000 | Schmaltz et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 * | 11/2004 | Cooper ............ A61B 17/00234 606/205 |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,654,431 B2 * | 2/2010 | Hueil ............ A61B 17/07207 227/181.1 |
| 7,658,312 B2 | 2/2010 | Vidal et al. |

(56) References Cited

U.S. PATENT DOCUMENTS

| | | |
|---|---|---|
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,864,010 B2 * | 10/2014 | Williams ......... A61B 17/07207 227/176.1 |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 * | 11/2018 | Cappola ................ A61B 90/90 |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 2002/0165562 A1 | 11/2002 | Grant et al. |
| 2003/0135204 A1 * | 7/2003 | Lee .................... B25J 9/104 606/1 |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 * | 1/2006 | Racenet ........... A61B 17/07207 227/176.1 |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0217706 A1 | 9/2006 | Lau et al. |
| 2006/0226196 A1 | 10/2006 | Hueil et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton et al. |
| 2008/0086114 A1 * | 4/2008 | Schmitz ................ A61B 17/00 606/1 |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0118707 A1 | 5/2011 | Burbank |
| 2011/0152879 A1 | 6/2011 | Williams |
| 2011/0174863 A1 | 7/2011 | Shelton, IV et al. |
| 2011/0251612 A1 | 10/2011 | Faller et al. |
| 2011/0251613 A1 | 10/2011 | Guerra et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 * | 1/2012 | Racenet ........... A61B 17/07207 227/175.1 |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1 | 1/2014 | Sims et al. |
| 2014/0100600 A1 | 4/2014 | Kendrick |
| 2014/0175152 A1 | 6/2014 | Hess et al. |
| 2014/0180286 A1 | 6/2014 | Marczyk et al. |
| 2014/0200596 A1 | 7/2014 | Weir et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |

(56) References Cited

U.S. PATENT DOCUMENTS

| | | |
|---|---|---|
| 2015/0173789 A1 | 6/2015 | Baxter, III et al. |
| 2015/0209037 A1 | 7/2015 | Kostrzewski et al. |
| 2015/0250530 A1* | 9/2015 | Manzo .............. A61B 18/1482 606/51 |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1* | 1/2018 | Hatanaka .......... A61B 17/07207 |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0015124 A1 | 1/2019 | Williams et al. |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0142531 A1 | 5/2019 | Wentworth et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0183686 A1 | 6/2022 | Wixey et al. |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |

FOREIGN PATENT DOCUMENTS

| | | |
|---|---|---|
| EP | 0641546 A1 | 3/1995 |
| EP | 1090592 A1 | 4/2001 |
| EP | 1728473 A1 | 12/2006 |
| EP | 1479346-B1 | 1/2007 |
| EP | 1621141 B1 | 7/2007 |
| EP | 1316290 B1 | 2/2012 |
| EP | 1754445 B1 | 10/2013 |
| EP | 3135225 A2 | 3/2017 |
| EP | 3158947 A1 | 4/2017 |
| EP | 3173029 A1 | 5/2017 |
| FR | 2828952 B1 | 12/2005 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

European Search Report (Corrected version) for Application No. EP19750317.0, mailed on Mar. 28, 2022, 26 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
International Search Report and Written Opinion for Application No. PCT/US2020/054568, mailed Jan. 29, 2021, 13 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US2020/025655, mailed Jul. 22, 2020, 8 pages.
International Search Report and Written Opinion for Application No. PCT/US19/17646, mailed on Apr. 16, 2019. 11 pages.

(56) References Cited

OTHER PUBLICATIONS

International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2020/020672, mailed Jun. 29, 2020, 10 pages.
International Search Report and Written Opinion for Application No. PCT/US2020/033481. mailed Sep. 3, 2020, 22 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

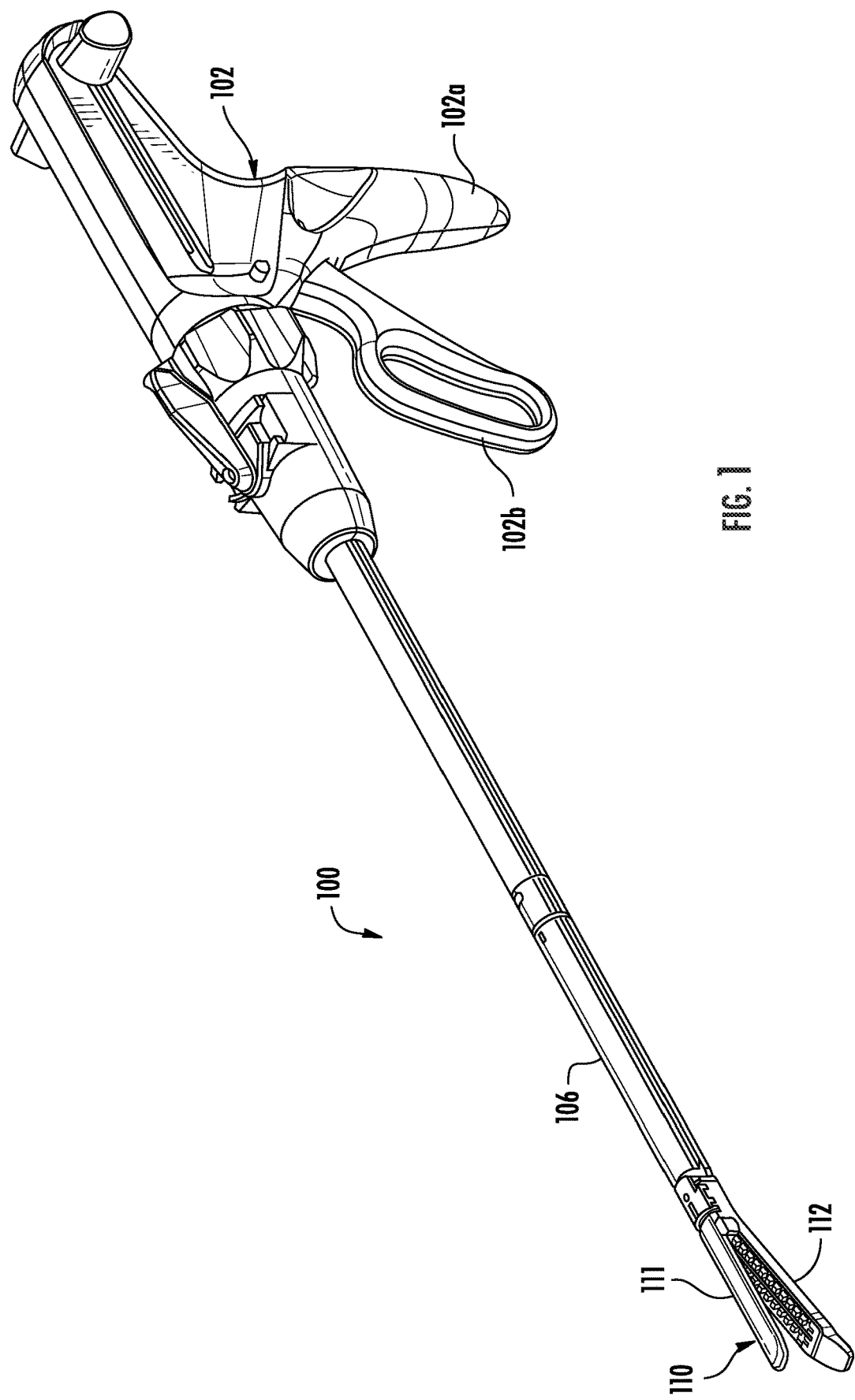

ACTUATION MECHANISMS FOR SURGICAL INSTRUMENTS

CROSS REFERENCE TO RELATED APPLICATIONS

This application is the National Stage of International Application No. PCT/US2019/064861 filed Dec. 6, 2019, which claims benefit of U.S. Provisional Application No. 62/783,460, filed Dec. 21, 2018, the entire disclosure of which is incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having an actuation mechanism that allows for taller staples and a more compact end effector.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms. A surgical instrument is mounted on each of the robotic arms. Operative communication between master controllers and associated robotic arm and instrument assemblies is typically achieved through a control system. The control system typically includes at least one processor that relays input commands from the master controllers to the associated robotic arm and instrument assemblies and back in the case of, for example, force feedback or the like. One example of a robotic surgical system is the DA VINCI™ system commercialized by Intuitive Surgical, Inc. of Sunnyvale, Calif.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912, 6,758,843, 6,246,200, and 5,800,423, the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. Nos. 6,702,805, 6,676,669, 5,855,583, 5,808,665, 5,445,166, and 5,184,601, the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide two or three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Conventional surgical clamping and cutting instruments typically include an end effector with a fixed jaw and a movable jaw that can be opened and closed relative to the fixed jaw. A staple cartridge is often designed to fit within one of the jaws of the end effector. The staple cartridge contains multiple rows of staple assemblies that each includes a staple and a staple driver, sometimes referred to as a staple pusher. The staple pusher holds the staple in place prior to use, and then drives the staple into tissue when the instrument is actuated. Prior to actuation of the staples, the jaws are in a "closed" position around the tissue. In this closed position, the jaws are typically parallel to each other such that the distance between the upper and lower jaws is a fixed dimension along the length of the jaws. This parallel tissue gap between the jaws places the jaws in close cooperative alignment for clamping, sealing and/or holding the tissue in place prior to stapling.

Depending on the clinical requirements of the procedure and/or the surgeon's preference, different types of staple cartridges may be desired. For example, certain staple cartridges have taller staples than others in the event that, for example, a stronger tissue seal is required. In other cases, shorter staples may be desired to avoid damage to collateral tissue in tightly confined spaces.

Conventional surgical clamping and cutting instruments typically have a drive member that is advanced through the staple cartridge to close the jaws and engage the staples, thereby driving the staples into tissue. An actuator, such as a cable or coil, advances the drive member distally through an internal channel in the central portion of the staple cartridge. One of the drawbacks with this design, however, is that the actuator coil must take up space in the central part of the staple cartridge. This forces the actual staples to be disposed laterally of this internal channel. Most staple cartridges are generally designed with a U-shape, a C-shape or similar curved cross-sectional shape to limit the col lateral damage to tissue as the instrument is maneuvered within the patient. This curved shape, however, means that the lateral portions of the staple cartridge are shorter than the central portion. Because the staples are forced into these lateral portions by the internal channel, the height of the staples that can be used within the staple cartridge is limited. Alternatively, the cross-sectional area of the staple cartridge must be made larger to accommodate taller staples.

Accordingly, while the new telesurgical systems and devices have proven highly effective and advantageous, still further improvements would be desirable. In general, it would be desirable to provide improved surgical instruments that are more compact and maneuverable to enhance the efficiency and ease of use of minimally invasive systems. More specifically, it would be beneficial to create improved drive members and/or actuation mechanisms for surgical clamping instruments that allow for taller staples and/or more compact end effectors.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical instruments having an elongate shaft and an end effector including first and second jaws configured to move relative to each other from an open position to a closed position. The instruments further include a drive member including a first portion that translates through a channel in the first jaw, and an actuation mechanism in contact with the first portion of the drive member. The actuation mechanism is configured to translate the drive member distally through the end effector.

In certain embodiments, the second jaw includes a staple cartridge with a plurality of staples for engaging tissue. The actuation mechanism advances the drive member through the first jaw (instead of through an internal channel in the staple cartridge as in conventional surgical stapling instruments). Eliminating the internal channel for the actuation mechanism from the staple cartridge provides more space in the cartridge for the staples. In certain embodiments, taller staples may be used with a staple cartridge having substantially the same cross-sectional area as conventional staple cartridges. In other embodiments, a staple cartridge with a smaller cross-sectional area may be designed for use with staples of the same height as conventional staples. In still other embodiments, a more compact instrument may be designed that also employs taller staplers. Thus, the present invention allows for the use of taller staples and/or a more compact and maneuverable instrument.

In a preferred embodiment, the actuation mechanism includes a cable or coil that applies a distal force to the first portion of the drive member. The coil is configured to pass through at least a portion of the channel in the first jaw to translate the drive member distally through the end effector. One of the advantages of the present invention is that a smaller coil diameter may be used when the coil runs through the first jaw (rather than the staple cartridge) because the first jaw is typically an anvil made of metal. Thus, the anvil is more structurally sound than the staple cartridge, which typically includes plastic pathways. Reducing the diameter of the coil also allows for the design of a more compact instrument.

In certain embodiments, the drive member is configured to engage the staples upon distal translation of the drive member through the staple cartridge and move the staples from an interior of the staple cartridge to an exterior of the staple cartridge. An actuator is operatively coupled to the actuation mechanism. In a preferred embodiment, the actuator includes a control device of a robotic surgical system.

In another aspect of the invention, the present disclosure further relates to a coupling device, such as a clevis, for mounting first and second jaws of an end effector to the distal end portion of a surgical instrument. The coupling device comprises a proximal end configured for coupling to the surgical instrument and a distal end configured for coupling to the end effector. The coupling device further includes a channel having a first end at a central portion of the proximal end of the coupling device and a second end at a peripheral portion of the distal end of the coupling device.

The clevis of the present disclosure is particularly beneficial with a surgical stapling instrument. The internal channel provides a passage for an actuation mechanism to advance or translate a drive member through, for example, the first jaw or anvil on the end effector. The channel has a proximal end in the central portion of the surgical instrument for coupling with the drive assembly of the instrument and receiving the actuation mechanism, e.g., a coil or cable. The channel curves to a peripheral portion of the instrument to allow the actuation mechanism to pass through the first jaw of the end effector. This configuration allows the actuation mechanism to advance the drive member through the first jaw (instead of through the staple cartridge as in conventional surgical stapling instruments), thereby eliminating the internal channel for the actuation mechanism from the staple cartridge and providing more space in the cartridge for the staples.

In another aspect of the invention, a surgical instrument comprises an elongate shaft with an internal passage and an end effector coupled to the shaft. The end effector includes a first fixed jaw and a second jaw configured to move relative to the fixed jaw from an open position to a closed position. The instrument further comprises an actuation mechanism configured to translate distally through at least a portion of the internal passage of the shaft and at least a portion of the channel in the fixed jaw.

In a preferred embodiment, the surgical instrument further includes a coupling device, such as a clevis or the like, between the shaft and the end effector. The coupling device defines a channel coupling the internal passage of the shaft with the channel of the end effector. The channel extends in a longitudinal direction and in a lateral or transverse direction relative to the shaft. In an exemplary embodiment, the channel curves from a substantially central portion relative to the elongate shaft to a substantially peripheral portion relative to the elongate shaft.

In certain embodiments, the surgical instrument further includes a joint assembly for articulating the end effector relative to the elongate shaft, wherein the coupling device is disposed between the joint assembly and the end effector. This minimizes the length between the joint assembly and the fixed jaw, resulting in a decrease in the distance needed to jog the coil up into the anvil, allowing for an overall reduction in the size of the surgical instrument.

In an exemplary embodiment, the surgical instrument further includes a drive member for engaging staples in a staple cartridge coupled to the second jaw. The actuation mechanism is in contact with the drive member to translate the drive member distally through at least a portion of the channel in the first jaw. The instrument may include actuator operatively coupled to the actuation mechanism. The actuator may include a control device of a robotic surgical system.

It is to be understood that both the foregoing general description and the following detailed description are exemplary and explanatory only and are not restrictive of the disclosure. Additional features of the disclosure will be set forth in part in the description which follows or may be learned by practice of the disclosure.

DESCRIPTION OF THE DRAWINGS

The above and other aspects, features, and advantages of the present surgical instruments will become more apparent in light of the following detailed description when taken in conjunction with the accompanying drawings in which:

FIG. 1 is a perspective view of a representative surgical instrument in accordance with the present disclosure;

DETAILED DESCRIPTION

Figure 1A:
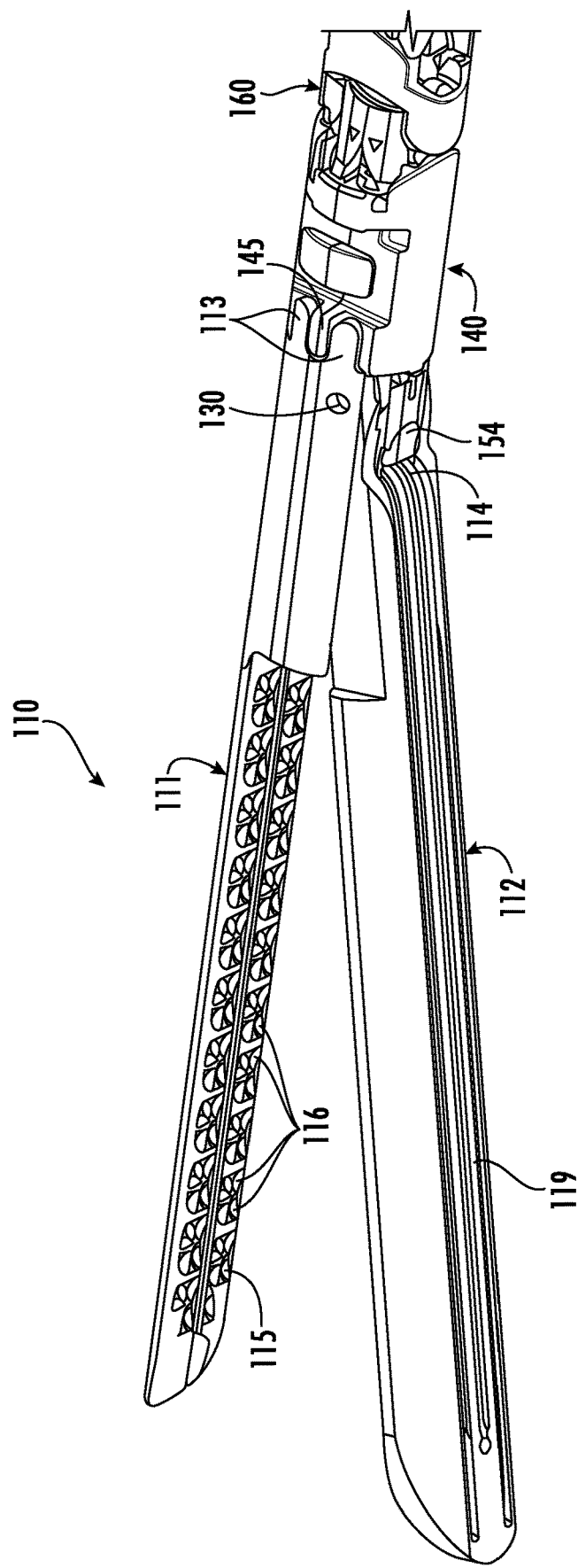
FIG. 1A is a perspective view of the distal end portion of the surgical instrument of FIG. 1.

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail.

While the following disclosure is presented with respect to a linear surgical stapler where staples are sequentially fired, it should be understood that the features of the presently described surgical instruments may be readily adapted for use in any type of surgical grasping, clamping, cutting, or sealing instruments, whether or not the surgical clamping and cutting instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery. Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

FIG. 1 is a perspective view of a representative surgical stapling instrument 100 in accordance with certain embodiments of the present disclosure having a handle assembly 102, and an end effector 110 mounted on an elongated shaft 106 of the surgical stapling instrument 100. End effector 110 includes a first jaw 111 and a second jaw 112. Handle assembly 102 includes a stationary handle 102a and a moveable handle 102b, which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S. Pub. No. 2014/0183244A1, the entire disclosure of which is incorporated by reference herein. The input couplers are drivingly coupled with one or more input members (not shown) that are disposed within the instrument shaft 106. The input members are drivingly coupled with the end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

FIG. 1A shows the distal end portion of surgical instrument 100, including an end effector 110 defining a longitudinal axis 1-1 and having a first jaw 111, a second jaw 112, a clevis 140 for mounting jaws 111, 112 to the instrument, and an articulation mechanism, such as wrist assembly 160. First jaw 111 includes an anvil 115 having staple-forming pockets 116. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, a fresh stapling cartridge (sometimes referred to as a reload) can be loaded into second jaw 112 and tissue may be positioned between the jaws 111, 112. In the closed position, jaws 111, 112 cooperate to clamp tissue such that the staple cartridge and the anvil 115 are in close cooperative alignment.

Figure 1B:
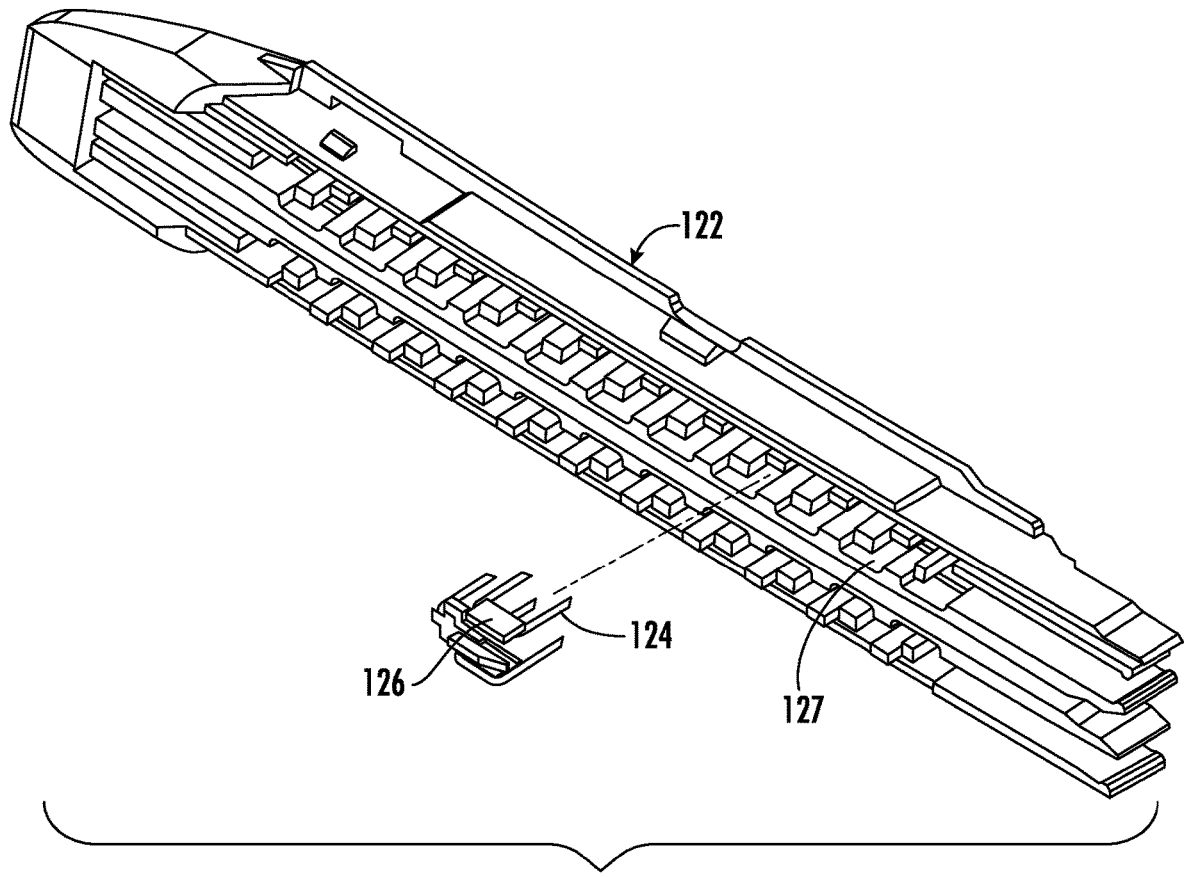
FIG. 1B is a bottom perspective view with parts separated of a representative staple cartridge for the surgical instrument of FIG. 1.
Figure 1C:
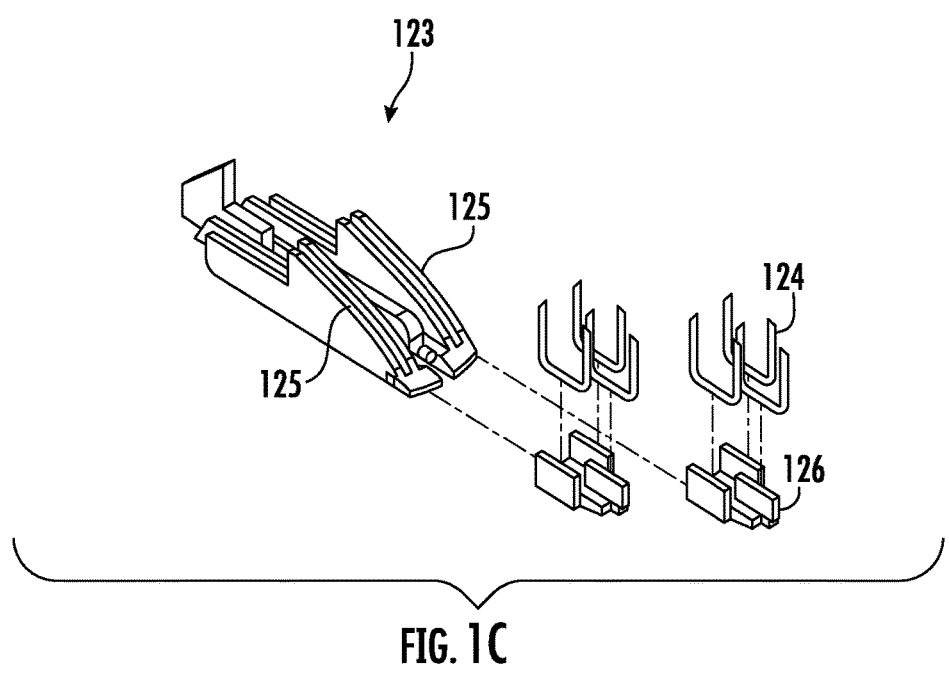
FIG. 1C shows an enlarged view of the cooperative relationship between a portion of a drive member and a plurality of staples which form part of the staple cartridge of FIG. 1B.

Referring now to FIGS. 1B and 1C, a representative staple cartridge 122 may include a plurality of staple assemblies, each comprising one or more staples 124 supported on corresponding staple drivers or pusher 126 provided within respective staple apertures 127 formed in cartridge 122. Of course, it should be recognized that the particular staple cartridge 122 shown in FIGS. 1B and 1C is representative only. Other embodiments of staple cartridge will be known to those of skill in the art. The staple assemblies each include at least one (preferably 2-4) staple pushers 126 removably coupled to at least one (preferably 2-4) staples 124. The staple assemblies are preferably arranged within apertures 127 such that staple pusher 126 is situated near a bottom surface of staple cartridge 122 and staples 124 have their legs facing a top surface of cartridge 122. As discussed above, the entire staple cartridge 122 can be loaded into a jaw of an end effector for use in surgery as described in more detail below. In certain embodiments, staple pusher(s) 126 include one or more supporting elements extending above their top surface for providing support to staples 124 when they are resting thereon. Of course, other suitable geometric designs of staple pusher 126 may be used to receive and hold staple 124 in accordance with the present invention. For example, pusher 126 may have a recess (not shown) for receiving staple 124, as is described in commonly-assigned, provisional patent application Ser. No. 62/855,371, filed May 31, 2019. Alternatively, pusher 126 may have a flatter upper surface (i.e., without a recess or pocket) that allows the backspan of staple 124 to rest thereon, as is described in commonly-assigned, provisional patent application Ser. No. 62,783,460, the complete disclosures of both of these applications are hereby incorporated by reference in their entirety for all purposes.

Cartridge 122 also may include a shuttle 123 having an inclined distal surface 125 that, upon distal movement, sequentially acts on staple pushers 126, camming them upwardly, thereby moving staples 124 into deforming contact with an anvil of a surgical instrument. Shuttle 123 may be part of a drive member 150 (FIGS. 6-8) described in more detail below. In certain embodiments, drive member 150 may also include a knife 128 configured to translate distally through a channel 119 in cartridge 122 and to sever clamped, stapled tissue. In embodiments, knife 128 may simply be a sharpened edge on drive member 150 rather than a distinct structure within the cartridge. Cartridge 122 may be removably received within a jaw of a surgical instrument or, in single use embodiments, may be manufactured as part of the jaw.

Figure 2:
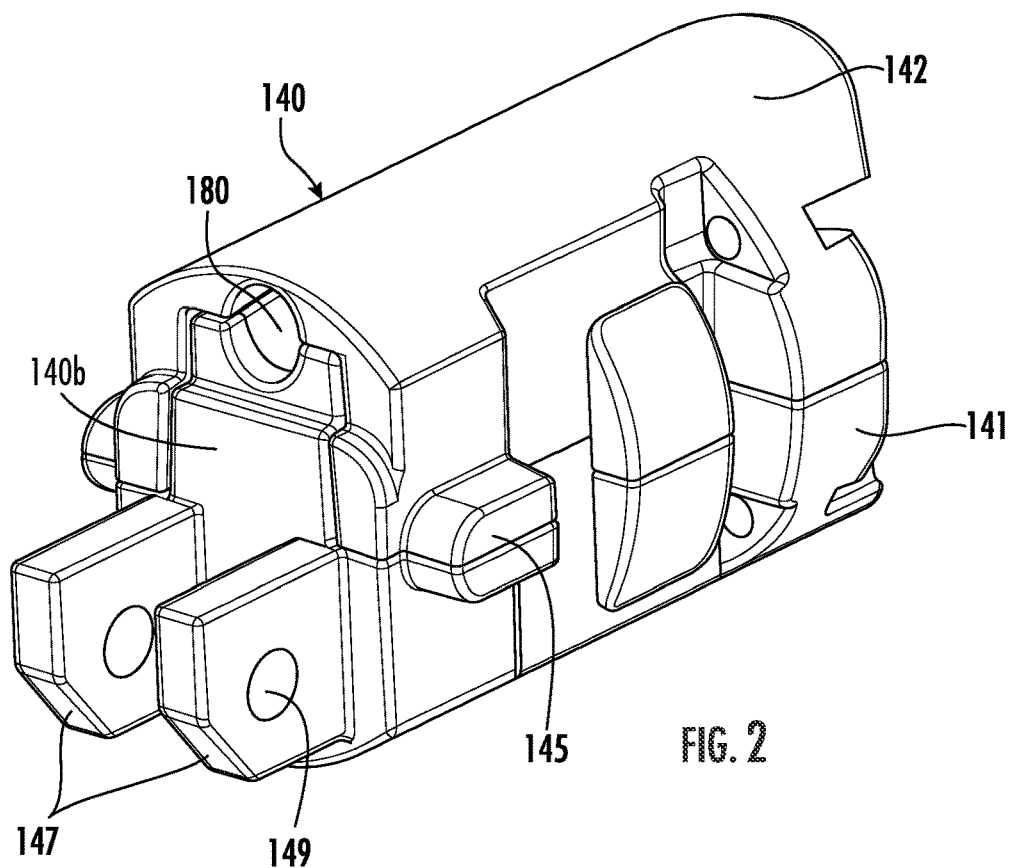
FIG. 2 is a perspective view of a coupling device or clevis of the surgical instrument of FIG. 1.
Figure 3:
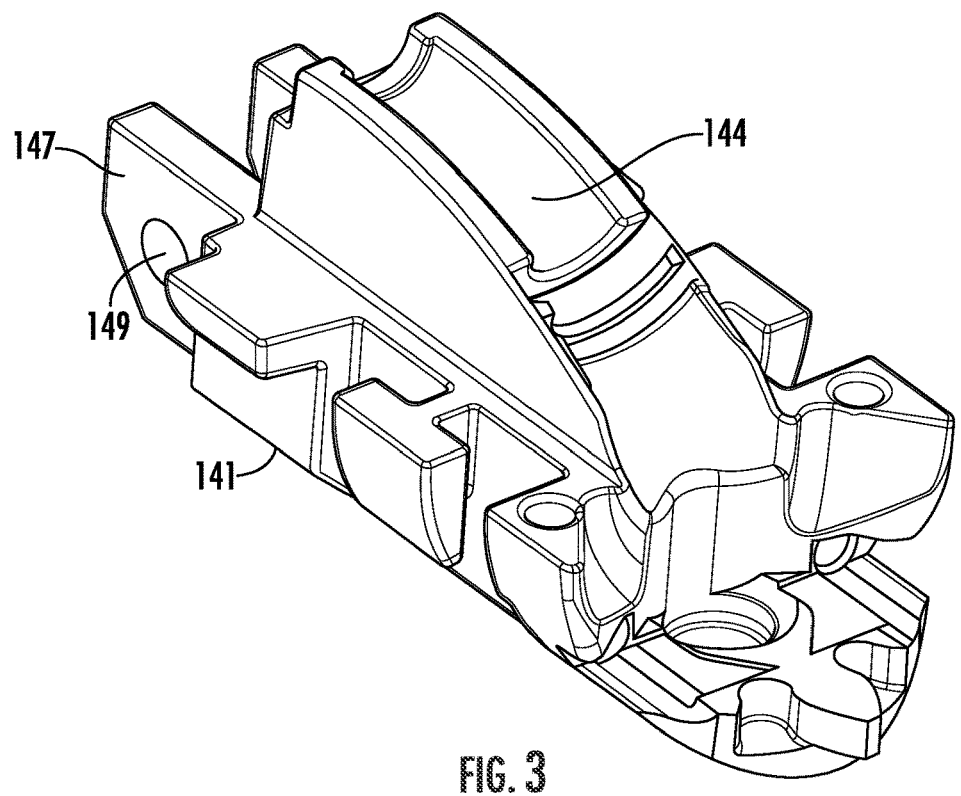
FIG. 3 is a perspective top view of the lower portion of the clevis shown in FIG. 2.
Figure 4:
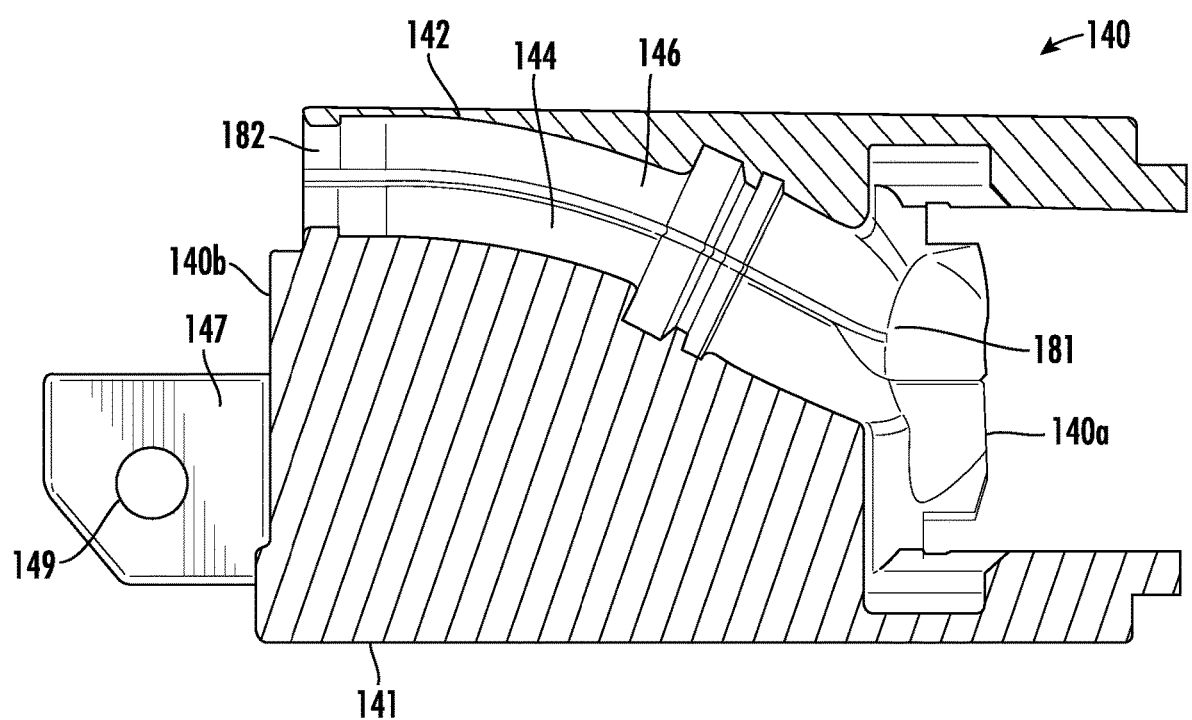
FIG. 4 is a cross-sectional side view of the clevis shown in FIG. 2.

In certain embodiments, jaws 111, 112 are attached to surgical instrument 100 via clevis 140. FIGS. 2-4 depict various views of a clevis 140 according to the present disclosure. Clevis 140 includes a proximal surface 140a and a distal surface 140b. Clevis 140 further includes an upper clevis portion 142 and a lower clevis portion 141 that cooperate when assembled to form protrusion 145 configured to engage tabs 113 of jaw 111 to securely mount jaw 111 in a fixed position on instrument 100 (see FIG. 1A). Lower clevis portion 141 includes a pair of distally extending arms 147 for supporting movable jaw 112. Arms 147 include opening 149 for receiving a pivot pin 130 defining a pivot axis around which jaw 112 pivots. Lower clevis portion 141 also includes ramped groove 144 configured to guide a portion of an actuation coil 120 (see FIG. 7A), emerging from wrist 160.

As best seen in FIG. 4, upper clevis portion 142 includes a complementary shaped ramped groove 146 that cooperates with ramped groove 144 of lower clevis portion 141 to form an enclosed channel 180 that guides coil 120 as it jogs upwards from wrist 160 towards distal surface 157 of upper shoe 152 of drive member 150. In embodiments, channel 180 may include a first end 181 at a central portion of proximal surface 140a and a second end 182 at a peripheral portion of distal surface 140b. In certain embodiments, enclosed channel 180 may be substantially "S" shaped. In other embodiments, channel 180 may be substantially concave in the direction facing lower jaw 112 and substantially convex in the direction facing upper jaw 111. Although shown as a two-part clevis, it should be understood that the clevis may be a unitary structure formed, for example, by molding, machining, 3-D printing, or the like.

Clevis 140 of the present disclosure provides a passage or channel 180 for an actuation coil 120 to advance or translate drive member 150 through fixed jaw 111 on end effector 110. Channel 180 has a proximal end in the central portion of the surgical instrument for coupling with the drive assembly of the instrument and receiving actuation coil 180. Channel 180 curves to a substantially peripheral portion of the instrument to allow actuation coil 180 to pass through fixed jaw 111 of end effector 110. This configuration allows the actuation mechanism to advance the drive member through the fixed jaw (instead of through the staple cartridge jaw as in conventional surgical stapling instruments), thereby eliminating the internal channel for the actuation mechanism from the staple cartridge and providing more space in the cartridge for the staples.

Figure 5:
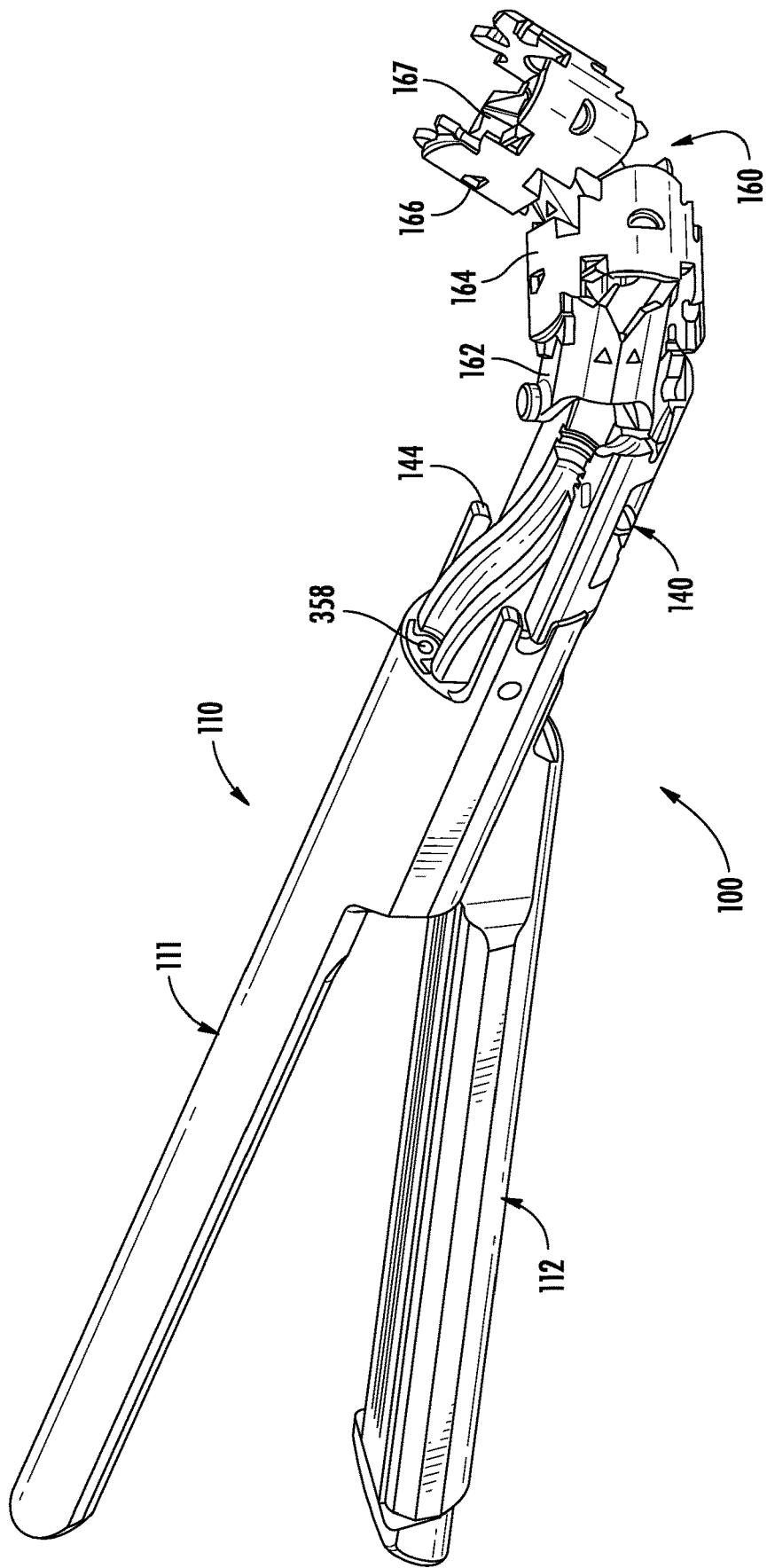
FIG. 5 is a perspective view of the end portion of an illustrative surgical instrument with parts removed.

Referring now to FIG. 5, end effector 110 may be articulated in multiple directions by an articulation mechanism. In embodiments, the articulation mechanism may be a wrist 160 as shown, although other articulation mechanisms are contemplated. In the representative embodiment, wrist 160 includes a plurality of articulation joints 162, 164, 166, etc. that define a bore 167 through which an actuation mechanism (in embodiments, coil 120 and drive cable 171, see FIG. 8) may pass. Upon exiting articulation wrist 160, coil 120 enters and passes through channel 180 of clevis 140, ultimately engaging proximal surface 153 of upper shoe 152 of drive member 150. Other articulation mechanisms are known by those skilled in the art that may substitute for wrist 160. Other exemplary articulating mechanisms are shown for example in U.S. Publication. No. 2015/0250530 and U.S. Provisional Patent Application Ser. No. 62/783,481, the complete disclosures of which are hereby incorporated by reference in their entirety for all purposes.

Figure 6:
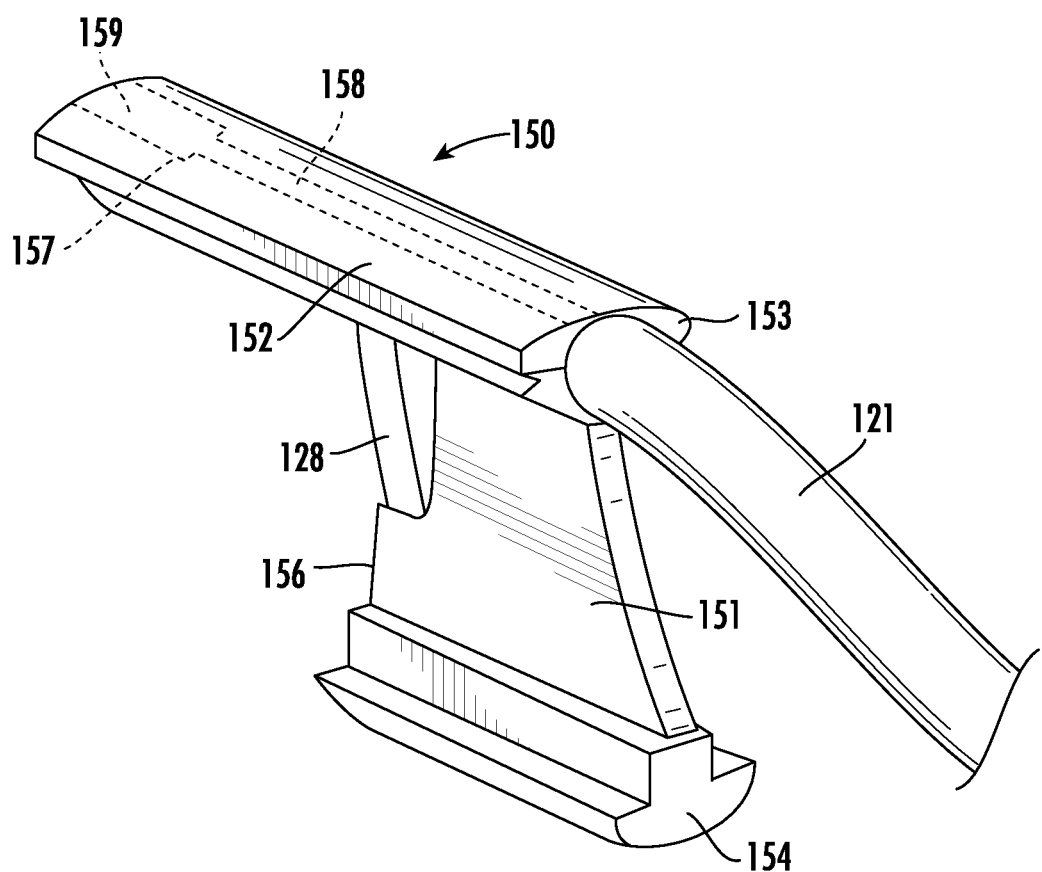
FIG. 6 illustrates a perspective view of a drive member and a coil in accordance with the illustrative surgical instrument of FIG. 1.
Figure 7A:
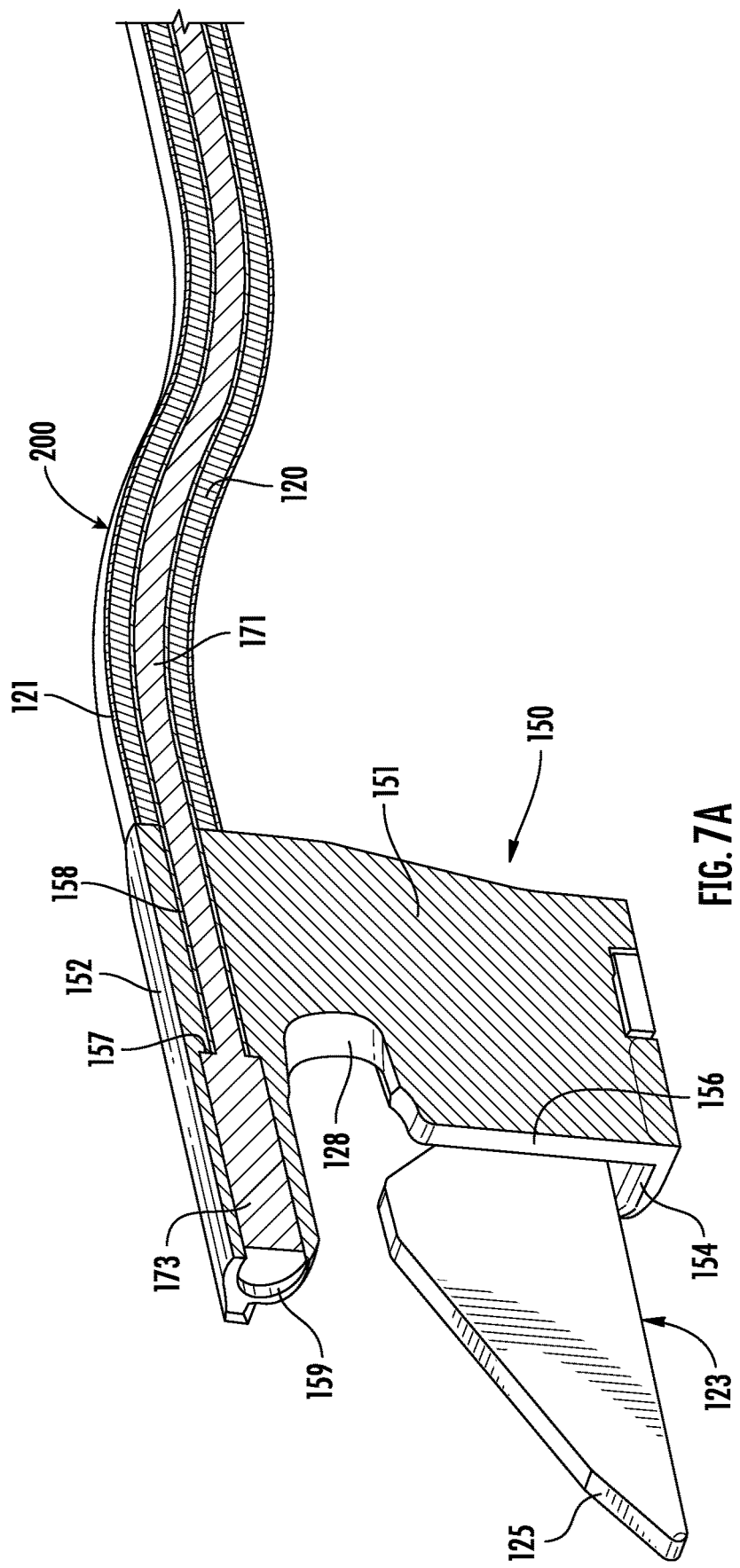
FIG. 7A is a cross-sectional perspective view of an actuation mechanism for a drive member in accordance for a surgical instrument according to the present disclosure.
Figure 7B:
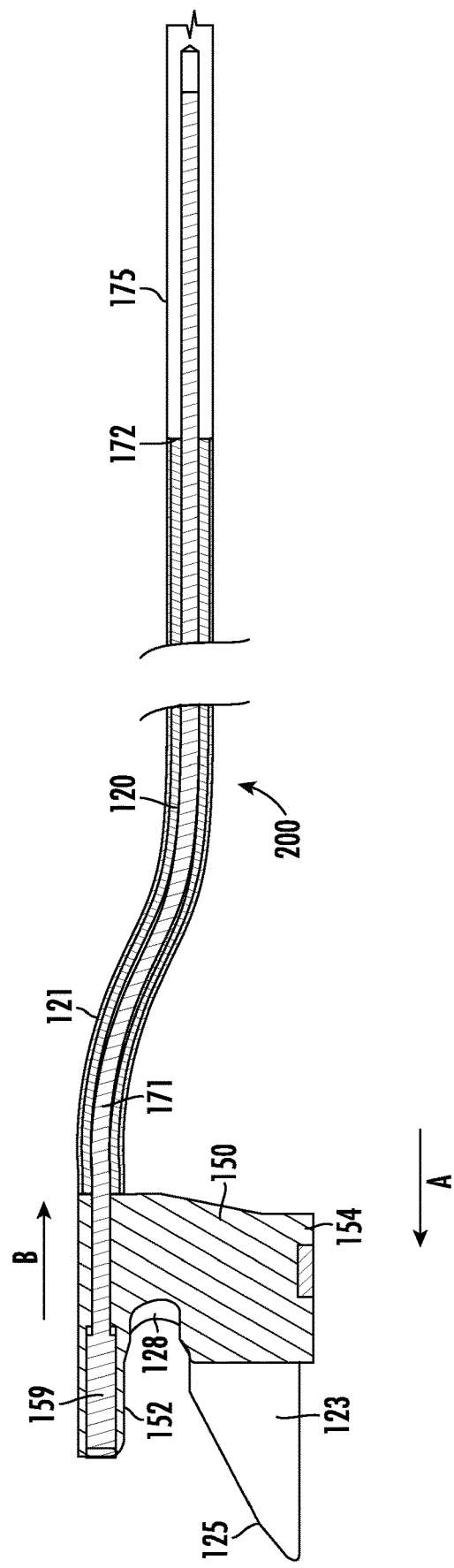
FIG. 7B is a cross-sectional side view of the actuation mechanism of FIG. 7A.

As shown in FIGS. 6, 7A and 7B, an illustrative drive member 150 may include a body 151, an upper shoe 152, a lower shoe 154, a central portion 156 and shuttle 123 having inclined distal surfaces 125. Actuation assembly 200 includes a drive cable 171, a coil 120, a sheath 121 surrounding coil 120, and a proximal drive rod 175. Drive cable 171 includes an enlarged distal end 173. Upper shoe 152 of drive member 150 includes bore 158 into which drive cables 171 are routed. Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL', polyparaphenylene terephthalamide materials such as KEVLAR™ commercially available from DuPont. Those of skill in the art may envision other suitable materials.

The proximal surface of upper shoe 152 is configured to be engaged by a coil 120 of actuation assembly 200 such that coil 120 may apply force to upper shoe 152 to advance drive member 150 distally. Proximal surface 153 of upper shoe 152 is configured to be engaged by a coil 120 of actuation assembly 200 such that coil 120 may apply force to upper shoe 152 to advance drive member 150 distally, i.e., in the direction of arrow "A" in FIG. 7B. A knife 128 may be formed on drive member 150 along the distal edge between upper shoe 152 and central portion 156. Enlarged distal end 173 of drive cable 171 resides within an enlarged distal portion 159 of bore 158 in upper shoe 152 of drive member 150, such that the proximal face 157 of enlarged distal end 173 may apply a retraction force on upper shoe 152 when the drive cable 171 is pulled proximally. Drive rod 175 is operationally connected to an actuator (e.g., input couplers 120), which allows distal translation and proximal retraction of actuation assembly 200. Those skilled in the art will recognize that in a manually actuated instrument, the actuator may be a movable handle, such as moveable handle 102b shown in FIG. 1; in a powered instrument the actuator may be a button (not shown) that causes a motor to act on the drive rod; and in a robotic system, the actuator may be a control device such as the control devices described below in connection with FIGS. 12 and 13. Any suitable backend actuation mechanism for driving the components of the surgical stapling instrument may be used. For additional details relating to exemplary actuation mechanisms using push/pull drive cables see, e.g., commonly owned International Application WO 2018/049217, the complete disclosure of which is hereby incorporated by reference in its entirety.

Figure 8:
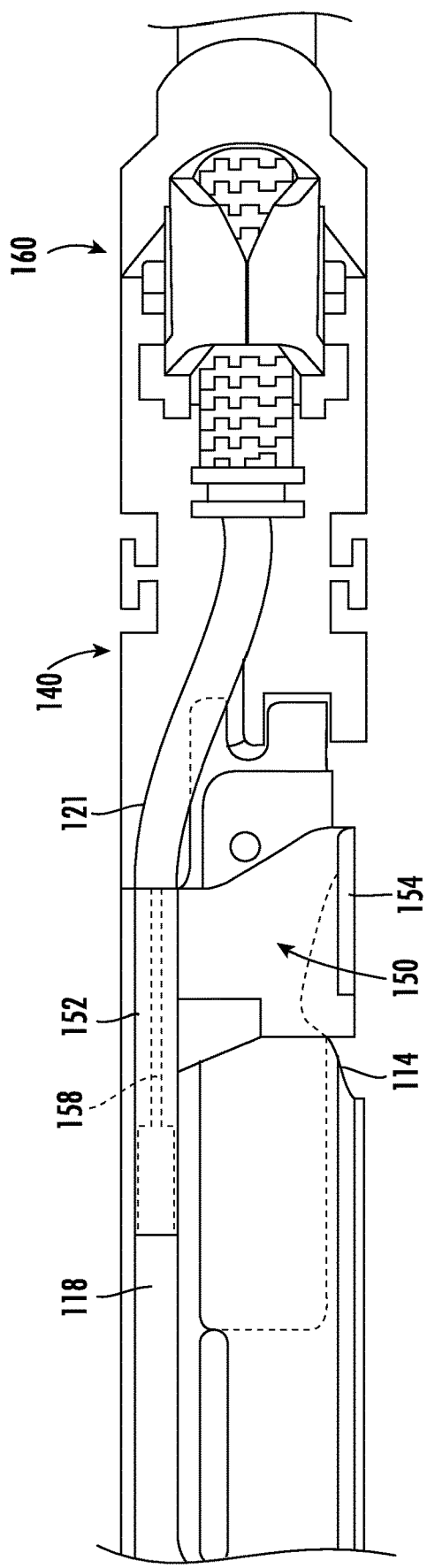
FIG. 8 is a partial cross-sectional side view of the end portion of an illustrative surgical instrument.

Upper shoe 152 of drive member 150 is substantially aligned with and translates through a channel 118 in fixed jaw 111, while lower shoe 154 of drive member 150 is substantially aligned with and translates through a channel 119 in jaw 112 and below jaw 112 (see FIG. 8). During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 7B) initially closing jaws 111,112 and then ejecting staples 124 from cartridge 122 to staple tissue. After stapling is complete, drive rod 175 may apply a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction (i.e., in the direction of arrow "B" in FIG. 7B). In certain embodiments, the surgical instrument may be designed such that the drive member 150 is not retracted in the proximal direction after the staples have been fired. One of ordinary skill in the art will appreciate that drive member 150, drive cable 171, and drive rod 175 all move in unison and remain in the same relative position to each other.

Upon actuation of the surgical instrument, drive member 150 is advanced distally through end effector 110 to move jaws 111, 112 from the open position to the closed position, after which shuttle 123 and knife 128 are advanced distally through cartridge 122 to staple and cut tissue grasped between jaws 111, 112. Of course, it will be recognized by those skilled in the art that drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through cartridge 122 and upper fixed jaw 111 and lower jaw 112 when the surgical stapling instrument is fired (e.g., actuated).

Drive cable 171 advances drive member 150 through fixed jaw 111 (instead of through the staple cartridge jaw as in conventional surgical stapling instruments). Eliminating the internal channel for the actuation mechanism from the staple cartridge provides more space in the cartridge for the staples. In certain embodiments, taller staples may be used with a staple cartridge having the same cross-sectional area. In other embodiments, a staple cartridge with a smaller cross-sectional area is designed for use with staples of the same height. In still other embodiments, a more compact instrument may be designed that still employs taller staplers. Thus, the present invention allows for the use of taller staples and a more compact and maneuverable instrument.

Figure 9A:
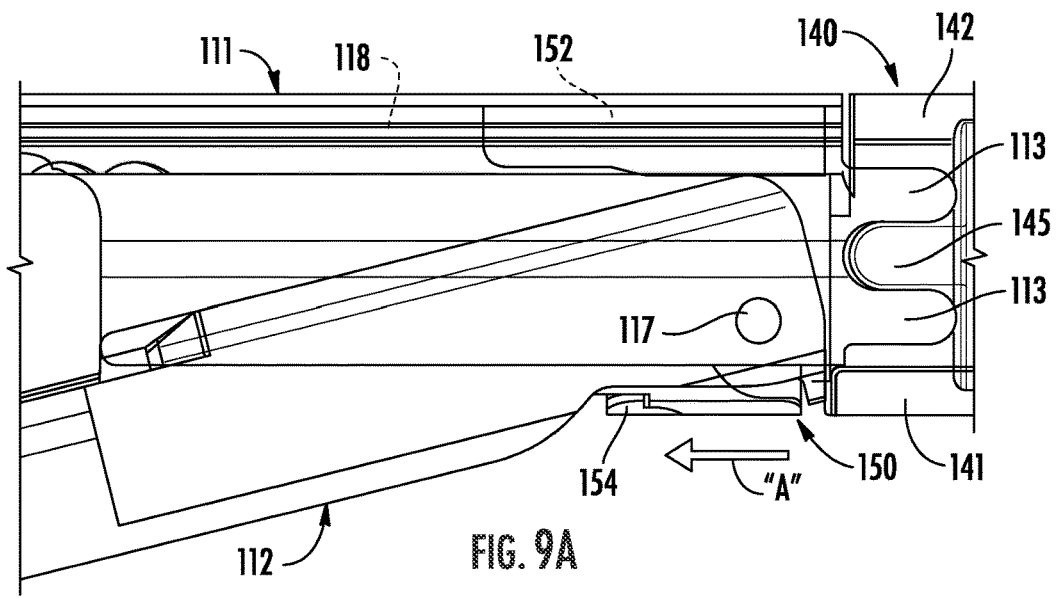
FIG. 9A shows a portion of a movable lower jaw of an illustrative surgical instrument in an open configuration.
Figure 9B:
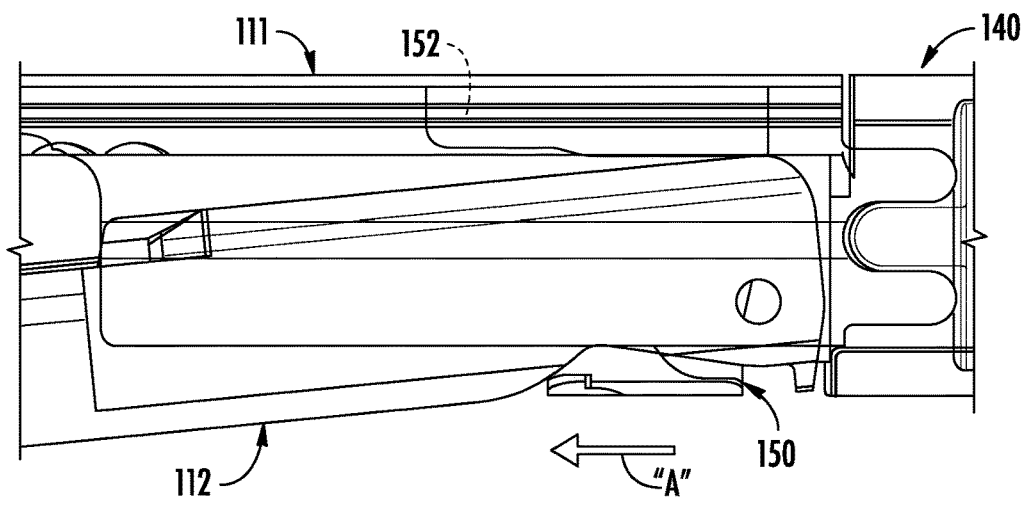
FIG. 9B shows the movable lower jaw of FIG. 9A pivoting towards a closed position.
Figure 9C:
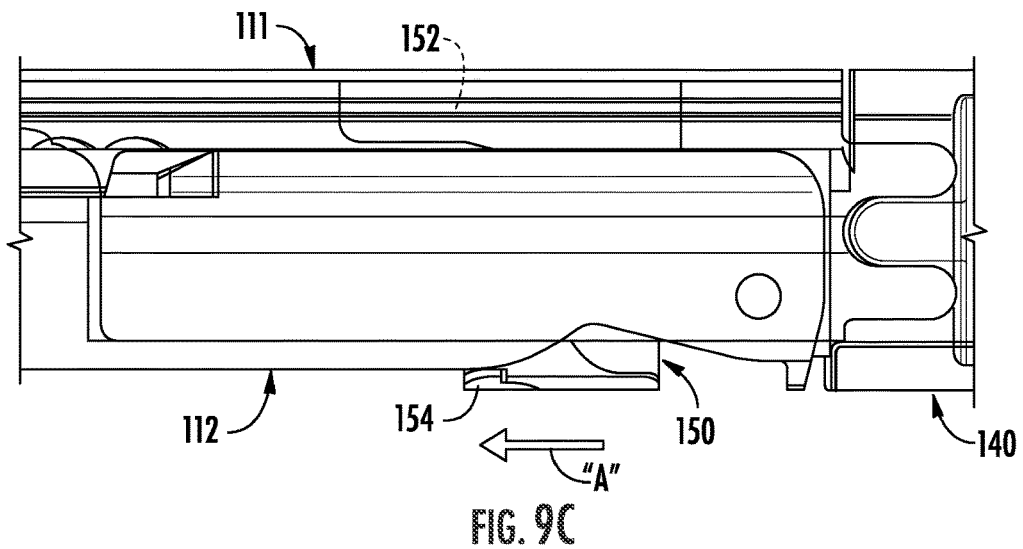
FIG. 9C shows the movable lower jaw of FIG. 9A in a closed position.

FIGS. 9A-C depict fixed jaw 111 and movable jaw 112 of illustrative surgical instrument 100 sequentially moving from an open configuration to a closed configuration. As shown in FIG. 9A, in the open configuration, drive member 150 is positioned proximally of cam surface 114 formed on movable jaw 112 (see also FIG. 1A). As drive member 150 translates in the distal direction "A" movable jaw 112 will rotate towards the closed position around pivot 117.

In FIG. 9B, drive member 150 has come into contact with cam surface 114 of movable jaw 112. As lower portion 154 of drive member 150 rides underneath cam surface 114, drive member 150 pushes movable jaw 112, causing it to pivot towards the closed position.

FIG. 9C illustrates jaws 111, 112 in the closed position. Drive member 150 has translated distally past cam surface 114. In this position, tissue is clamped, and further advancement of the drive member will sever and staple tissue.

Figure 10A:
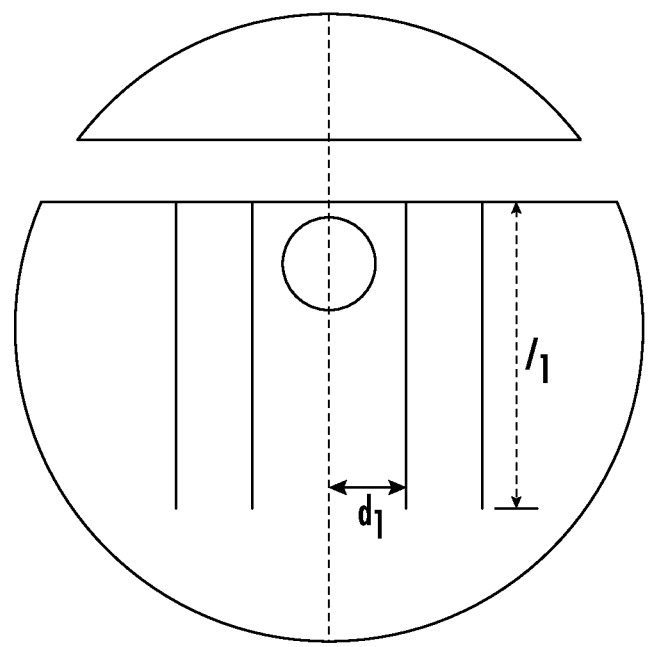
FIG. 10A depicts a diagrammatic view of a cross section of a known surgical instrument having an actuation member that passes through a staple cartridge.

FIG. 10A illustrates a cross section of a known surgical stapling instrument having a coil that passes through the staple cartridge. The length of each staple is represented by "$L_1$" while the distance between the cut line and the center row of staples is represented by "$d_1$". As shown, the staple cartridge typically has a U-shape, C-shape or similarly curved cross-sectional shape to minimize collateral damage to tissue when the surgical instrument is being maneuvered within the patient.

Figure 10B:
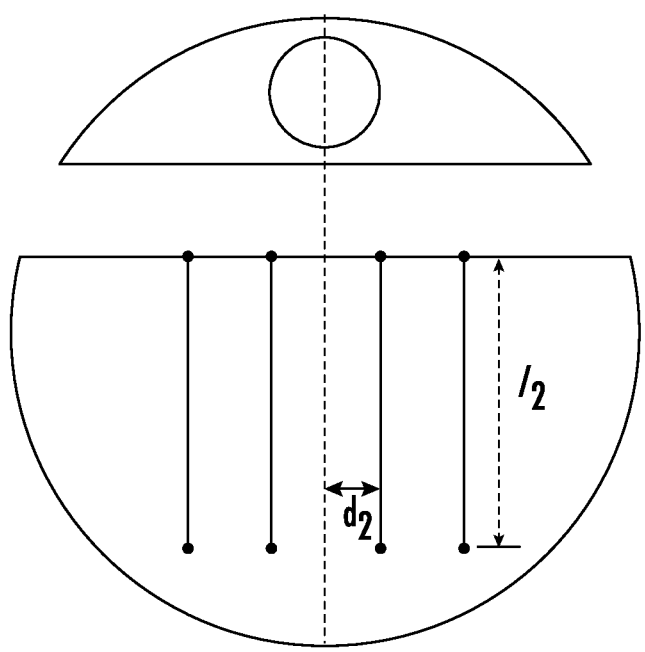
FIG. 10B depicts a diagrammatic view of a cross section of a surgical instrument in accordance with the present disclosure having an actuation member that passes through the anvil.

FIG. 10B illustrates a cross section of an illustrative surgical stapling instrument in accordance with the present disclosure, having a coil that passes through the fixed jaw (in this case the anvil). As shown, the length of each staple is represented by "$L_2$" while the distance between the cut line and the center row of staples is represented by "$d_2$". Eliminating the internal channel for the coil in the staple cartridge allows the staples to be disposed closer to the cut line (i.e., $d_2$ is smaller than $d_1$). Moving the staples closer to the cut line (i.e., closer to the center of the staple cartridge) provides more space in the cartridge to accommodate taller staples. Alternatively, the staple cartridge may be designed with a smaller overall cross-sectional area (with staples of the same height). Additionally, a smaller coil diameter may be used when the coil runs through the fixed jaw rather than the cartridge because a fixed anvil is typically made of metal and is therefore more structurally sound than the cartridge which typically includes plastic pathways.

Figure 11:
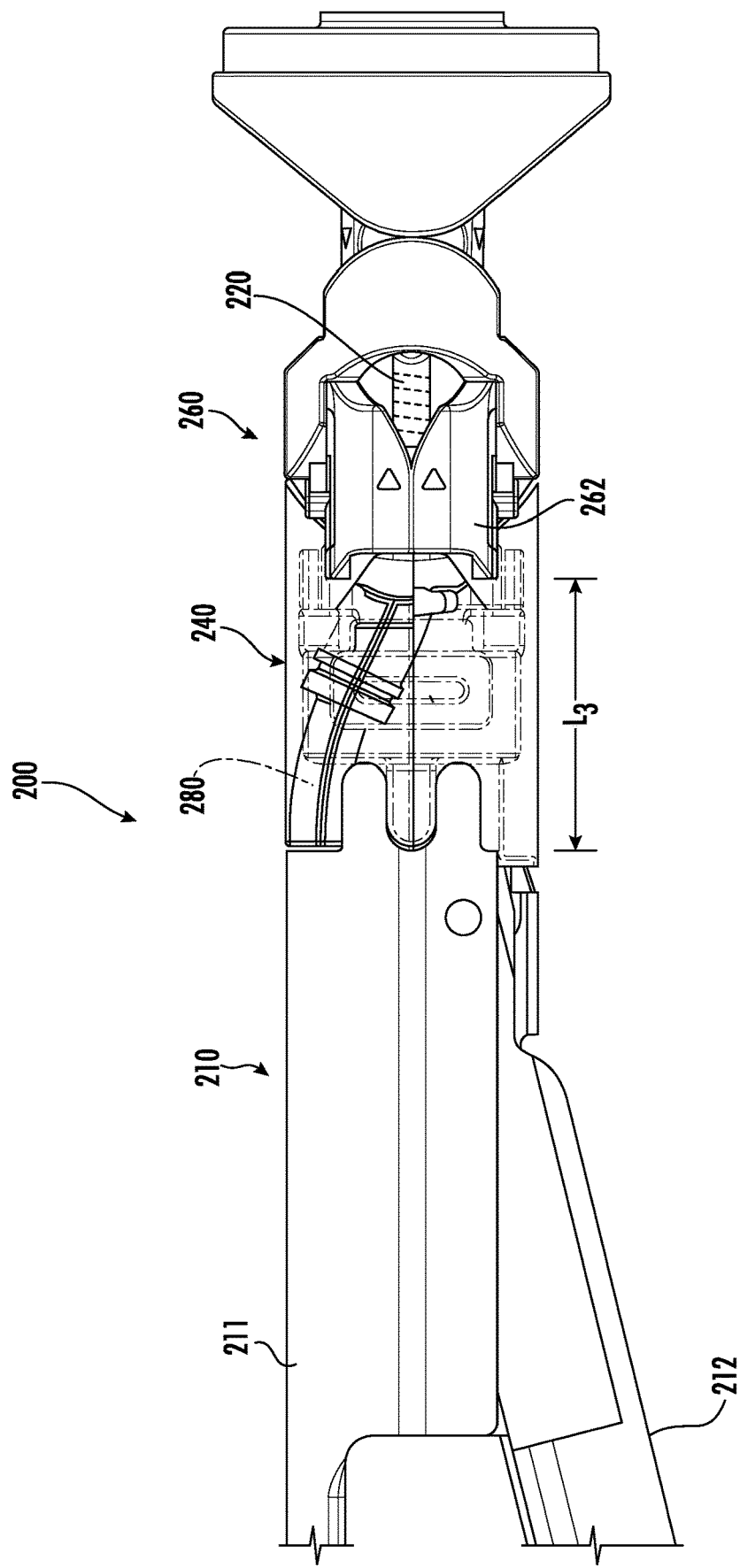
FIG. 11 is a side, partial cross-sectional view of a portion of a surgical instrument in accordance with another embodiment of the present disclosure.

FIG. 11 depicts a partial cross-sectional side view of an alternate embodiment of an illustrative surgical instrument 200 including an end effector 210 having jaws 211,212, a clevis 240, wrist 260, and a coil 220 that begins to jog upwards in a distal portion of a distal articulation joint 262 before passing through channel 280 in clevis 240. In this embodiment, clevis 240 is positioned distal of articulation joint 262 between the joint and end effector 210. The design of the embodiment of FIG. 11 minimizes the length $L_3$ between distal articulation joint 262 and fixed jaw 211 as compared to the illustrative surgical instrument 100. This results in a decrease in the distance needed to jog the coil up into the anvil, allowing for an overall reduction in size of the surgical stapling instrument.

Figure 12:
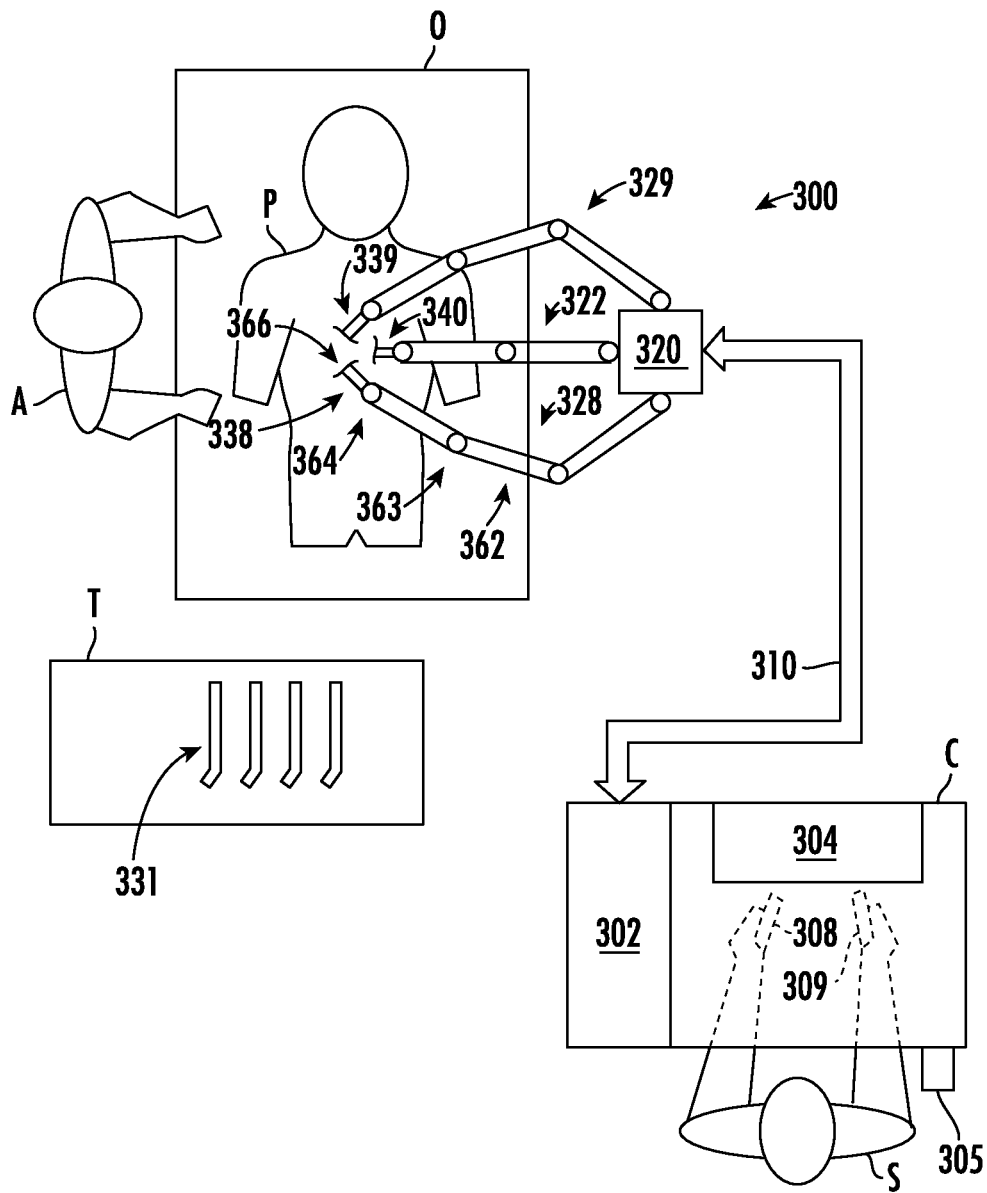
FIG. 12 illustrates a top view of an operating room employing a robotic surgical system utilizing aspects of the present invention.

FIG. 12 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," the complete disclosures of which are hereby incorporated herein by reference in their entirety for all purposes.

Figure 13:
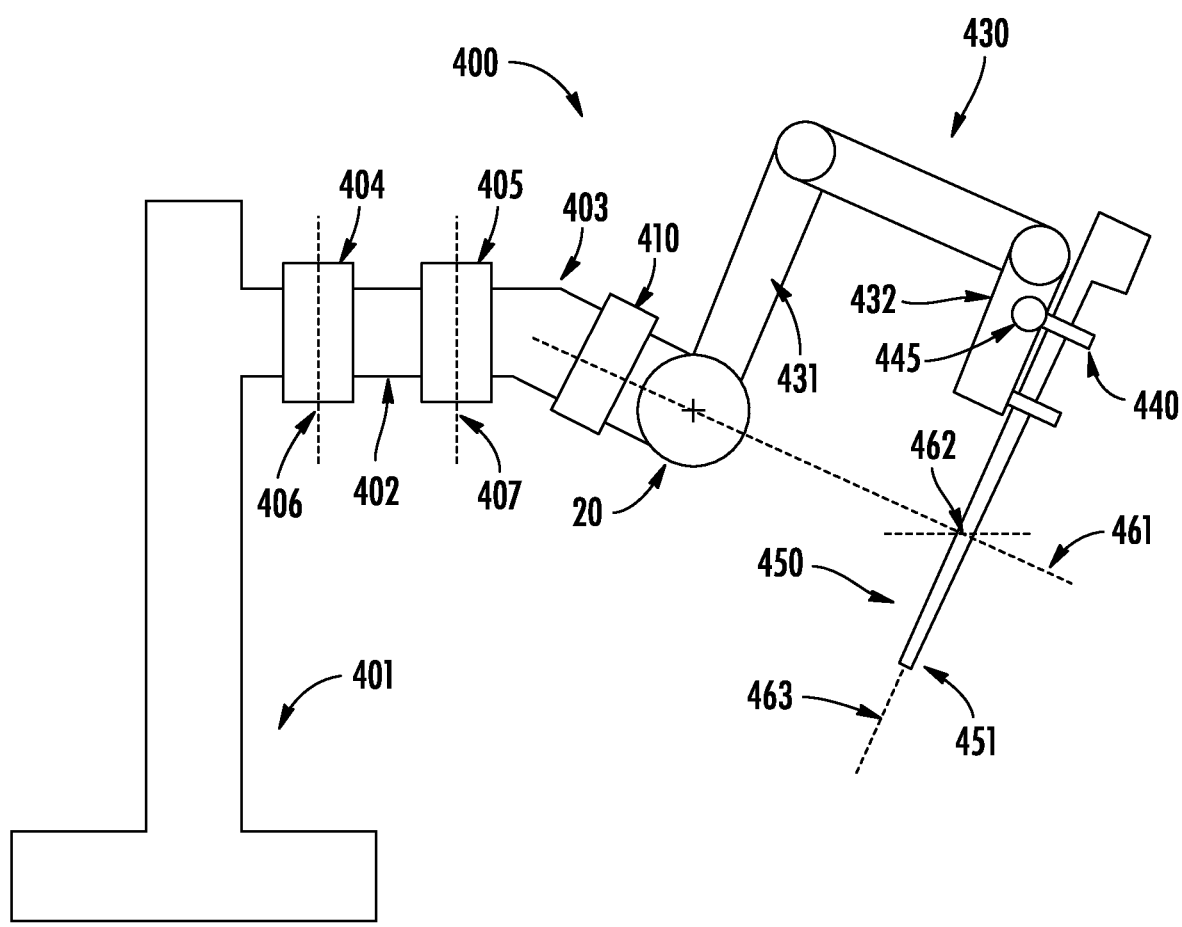
FIG. 13 illustrates a simplified side view of a robotic arm assembly that is usable with various aspects of the present invention.

FIG. 13 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358,074, and 9,452,019, the complete disclosures of which are hereby incorporated by reference in their entirety for all purposes.

While several embodiments have been shown in the drawings, it is not intended that the disclosure be limited thereto, as it is intended that the disclosure be as broad in scope as the art will allow and that the specification be read likewise. Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument comprising:
    an elongate shaft with an internal passage;
    an end effector coupled to the shaft and including a first jaw and a second jaw configured to move relative to each other from an open position to a closed position, the first jaw having a channel disposed laterally outward from the internal passage of the shaft and the second jaw being configured to receive a staple cartridge;
    a coupling device coupling the shaft with the end effector and having an internal channel, wherein the internal channel curves laterally outward from a first proximal end coupled to the internal passage of the shaft to a second distal end coupled to the channel in the first jaw;
    a drive member configured to translate distally through at least a portion of the channel of the first jaw; and
    a coil extending through the internal channel of the coupling device, the coil curving from the first proximal end of the coupling device to the second distal end of the coupling device to apply a force to the drive member.

2. The surgical instrument of claim 1, wherein the internal channel of the coupling device extends in a longitudinal direction and in a lateral direction relative to the shaft.

3. The surgical instrument of claim 2 further comprising a joint assembly for articulating the end effector relative to the elongate shaft, wherein the coupling device is disposed between the joint assembly and the end effector.

4. The surgical instrument of claim 1, wherein the coil is configured to pass through at least a portion of the channel in the first jaw to translate the drive member distally through the end effector.

5. The surgical instrument of claim 1, wherein the first jaw includes an anvil.

6. The surgical instrument of claim 1, wherein the coil extends through a bore formed in the drive member.

7. The surgical instrument of claim 1 further comprising a staple cartridge removably coupled to the second jaw and housing a plurality of staples, wherein the drive member is configured to engage the staples upon distal translation of the drive member through the staple cartridge and move the staples from an interior of the staple cartridge to an exterior of the staple cartridge.

8. The surgical instrument of claim 1 further comprising an actuator operatively coupled to the coil, wherein the actuator includes a control device of a robotic surgical system.

9. A surgical instrument comprising:
  an elongate shaft having a longitudinal axis;
  an end effector including a first jaw and a second jaw configured to move relative to each other between an open position and a closed position;
  a coupling device coupling the shaft with the end effector;
  a staple cartridge coupled to the second jaw;
  a drive member configured to translate distally through the end effector, the drive member including a first portion that translates through a channel in the first jaw; and
  a coil in contact with the first portion of the drive member to translate the drive member distally through the first jaw, wherein the coil passes through the coupling device and comprises a first portion oriented substantially parallel to the longitudinal axis of the shaft, a second curved portion, and a third portion oriented substantially parallel to the longitudinal axis of the shaft and laterally outward from the first portion.

10. The surgical instrument of claim 9, wherein the staple cartridge houses a plurality of staples, and wherein the drive member is configured to engage the staples upon distal translation of the drive member through the staple cartridge.

11. The surgical instrument of claim 9, further comprising an actuator operatively coupled to the coil.

12. The surgical instrument of claim 11, wherein the actuator includes a control device of a robotic surgical system.

13. The surgical instrument of claim 9, wherein the first jaw is fixed relative to the shaft and the second jaw is movable relative to the shaft and the first jaw.

* * * * *